United States Patent
Trusty et al.

(10) Patent No.: US 12,075,984 B2
(45) Date of Patent: Sep. 3, 2024

(54) STEREOSCOPIC ENDOSCOPE WITH CRITICAL STRUCTURE DEPTH ESTIMATION

(71) Applicant: Cilag GmbH International, Zug (CH)

(72) Inventors: Robert M. Trusty, Cincinnati, OH (US); Dillon C. Karg, San Jose, CA (US)

(73) Assignee: Cilag GmbH International, Zug (CH)

( * ) Notice: Subject to any disclaimer, the term of this patent is extended or adjusted under 35 U.S.C. 154(b) by 139 days.

(21) Appl. No.: 17/375,333

(22) Filed: Jul. 14, 2021

(65) Prior Publication Data
US 2023/0020780 A1   Jan. 19, 2023

(51) Int. Cl.
| A61B 1/313 | (2006.01) |
| A61B 1/00 | (2006.01) |
| A61B 1/05 | (2006.01) |
| A61B 1/06 | (2006.01) |

(52) U.S. Cl.
CPC ............ *A61B 1/313* (2013.01); *A61B 1/0005* (2013.01); *A61B 1/05* (2013.01); *A61B 1/0627* (2022.02); *A61B 1/0655* (2022.02)

(58) Field of Classification Search
CPC ....... A61B 1/313; A61B 1/3132; A61B 1/014; A61B 1/043; A61B 1/045; A61B 1/00147; A61B 1/00172; A61B 1/00045; A61B 1/0005; A61B 1/00009; A61B 1/05; A61B 1/0627; A61B 1/0655
See application file for complete search history.

(56) References Cited

U.S. PATENT DOCUMENTS

| 9,274,047 B2 | 3/2016 | Velten et al. |
| 9,552,660 B2 * | 1/2017 | Tripathi ................ G06T 19/20 |
| 9,718,190 B2 * | 8/2017 | Larkin ................ B25J 9/1694 |
| 9,901,408 B2 * | 2/2018 | Larkin ............... A61B 1/00193 |
| 10,008,017 B2 * | 6/2018 | Itkowitz ................ A61B 34/37 |
| 11,033,182 B2 | 6/2021 | Hansen et al. |
| 11,039,734 B2 | 6/2021 | Hansen et al. |

(Continued)

FOREIGN PATENT DOCUMENTS

EP    3845173 A1    7/2021

OTHER PUBLICATIONS

U.S. Appl. No. 17/375,281.

(Continued)

*Primary Examiner* — Ryan N Henderson
(74) *Attorney, Agent, or Firm* — Frost Brown Todd LLP

(57) ABSTRACT

A surgical visualization system comprises: (a) an endoscope comprising: (i) a shaft comprising a distal end, wherein the distal end is configured to be inserted into a cavity of a patient, (ii) a camera positioned at the distal end of the shaft for visualizing a first structure below a tissue surface within the cavity when the distal end is inserted into the cavity, wherein the camera defines a line of sight, wherein the camera is configured to be swept over the first structure; and (b) a processor in operative communication with the camera of the endoscope, wherein the processor is configured to: (i) monitor at least one sweep parameter when the camera is swept over the first structure, and (ii) estimate a depth of the first structure below the tissue surface based on the monitored at least one sweep parameter.

20 Claims, 9 Drawing Sheets

(56) References Cited

U.S. PATENT DOCUMENTS

| | | | |
|---|---|---|---|
| 2016/0015473 A1* | 1/2016 | Frimer | A61B 1/00006 606/130 |
| 2017/0251900 A1* | 9/2017 | Hansen | A61B 1/3132 |
| 2017/0354469 A1* | 12/2017 | Kogan | B25J 9/1682 |
| 2018/0228343 A1* | 8/2018 | Seeber | A61B 34/35 |
| 2019/0150719 A1* | 5/2019 | Jarrahi | G01J 3/42 |
| 2019/0274524 A1* | 9/2019 | Nagao | A61B 1/00 |
| 2020/0015898 A1 | 1/2020 | Scheib et al. | |
| 2020/0015899 A1 | 1/2020 | Scheib et al. | |
| 2020/0015907 A1 | 1/2020 | Scheib | |
| 2020/0015924 A1 | 1/2020 | Scheib et al. | |
| 2020/0015925 A1* | 1/2020 | Scheib | A61B 5/6844 |
| 2020/0125236 A1 | 4/2020 | Palushi et al. | |
| 2020/0289230 A1 | 9/2020 | Denlinger et al. | |
| 2021/0030484 A1* | 2/2021 | Tadano | A61B 34/20 |
| 2021/0196098 A1* | 7/2021 | Shelton, IV | A61B 1/045 |
| 2021/0196108 A1* | 7/2021 | Shelton, IV | A61B 1/046 |
| 2021/0196109 A1* | 7/2021 | Shelton, IV | A61B 90/30 |
| 2021/0196381 A1* | 7/2021 | Eckert | A61B 17/3205 |
| 2021/0196382 A1* | 7/2021 | Mumaw | A61B 90/37 |
| 2021/0196383 A1* | 7/2021 | Shelton, IV | G16H 20/40 |
| 2021/0196384 A1* | 7/2021 | Shelton, IV | A61B 34/10 |
| 2021/0196385 A1* | 7/2021 | Shelton, IV | A61B 1/0676 |
| 2021/0196386 A1* | 7/2021 | Shelton, IV | G16H 20/40 |
| 2021/0196423 A1* | 7/2021 | Shelton, IV | A61B 90/361 |
| 2021/0196424 A1* | 7/2021 | Shelton, IV | A61B 34/25 |
| 2021/0196425 A1* | 7/2021 | Shelton, IV | G16H 40/63 |
| 2021/0199557 A1* | 7/2021 | Shelton, IV | G06T 7/521 |

OTHER PUBLICATIONS

U.S. Appl. No. 17/375,593.

U.S. Appl. No. 17/375,615.

Frangi, Alejandro F., et al. "Multiscale vessel enhancement filtering." *International conference on medical image computing and computer-assisted intervention.* Springer, Berlin, Heidelberg, 1998.

Pennec, Xavier, Pascal Cachier, and Nicholas Ayache. "Understanding the "demon's algorithm": 3D non-rigid registration by gradient descent." *International Conference on Medical Image Computing and Computer-Assisted Intervention.* Springer, Berlin, Heidelberg, 1999. pp. 597-606.

Xue, Tianfan, et al. "A computational approach for obstruction-free photography." *ACM Transactions on Graphics (TOG)* 34.4 (2015): 1-11.

U.S. Appl. No. 17/375,281, entitled "Scene Adaptive Endoscopic Hyperspectral Imaging System," Filed Jul. 14, 2021.

U.S. Appl. No. 17/375,593, entitled "Endoscope with Synthetic Aperture Multispectral Camera Array," filed Jul. 14, 2021.

U.S. Appl. No. 17/375,615, entitled "Endoscope with Source and Pixel Level Image Modulation for Multispectral Imaging," filed Jul. 14, 2021.

International Search Report and Written Opinion dated Oct. 6, 2022, for International Application No. PCT/IB2022/056414, 12 pages.

* cited by examiner

STEREOSCOPIC ENDOSCOPE WITH CRITICAL STRUCTURE DEPTH ESTIMATION

BACKGROUND

Surgical systems may incorporate an imaging system, which may allow the clinician(s) to view the surgical site and/or one or more portions thereof on one or more displays such as a monitor. The display(s) may be local and/or remote to a surgical theater. An imaging system may include a scope with a camera that views the surgical site and transmits the view to a display that is viewable by the clinician. Scopes include, but are not limited to, laparoscopes, robotic laparoscopes, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems may be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

Examples of surgical imaging systems are disclosed in U.S. Pat. Pub. No. 2020/0015925, entitled "Combination Emitter and Camera Assembly," published Jan. 16, 2020, issued as U.S. Pat. No. 11,754,712 on Sep. 12, 2023; U.S. Pat. Pub. No. 2020/0015899, entitled "Surgical Visualization with Proximity Tracking Features," published Jan. 16, 2020, now abandoned; U.S. Pat. Pub. No. 2020/0015924, entitled "Robotic Light Projection Tools," published Jan. 16, 2020, now abandoned; and U.S. Pat. Pub. No. 2020/0015898, entitled "Surgical Visualization Feedback System," published Jan. 16, 2020, issued as U.S. Pat. No. 11,571,205 on Feb. 7, 2023. The disclosure of each of the above-cited U.S. patents and patent applications is incorporated by reference herein.

While various kinds of surgical instruments and systems have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
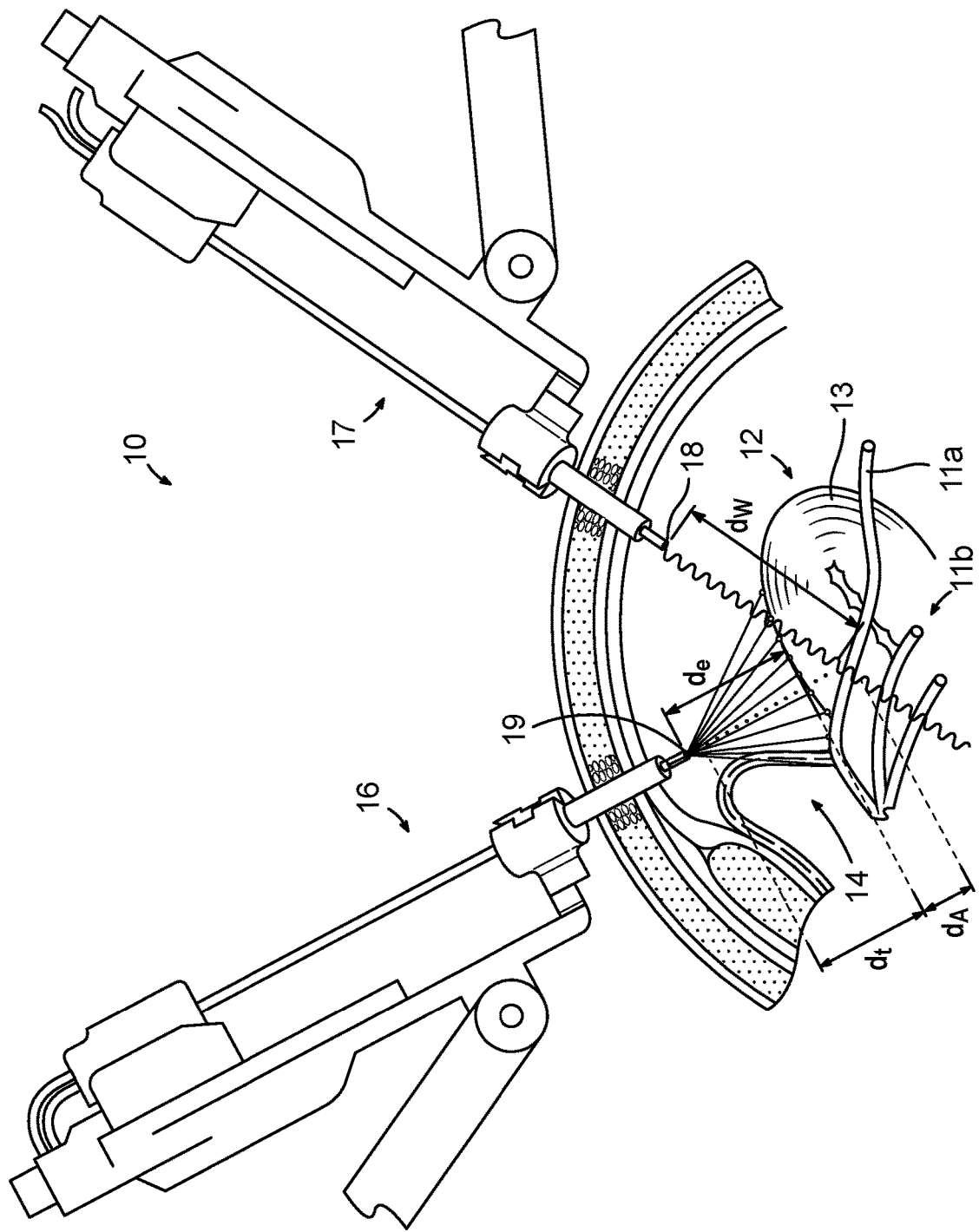
FIG. 1 depicts a schematic view of an exemplary surgical visualization system including an imaging device and a surgical device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

Similarly, the phrase "based on" should be understood as referring to a relationship in which one thing is determined at least in part by what it is specified as being "based on." This includes, but is not limited to, relationships where one thing is exclusively determined by another, which relationships may be referred to using the phrase "exclusively based on."

I. Exemplary Surgical Visualization System

FIG. 1 depicts a schematic view of a surgical visualization system (10) according to at least one aspect of the present disclosure. The surgical visualization system (10) may create a visual representation of a critical structure (11a, 11b) within an anatomical field. The surgical visualization system (10) may be used for clinical analysis and/or medical intervention, for example. In certain instances, the surgical visualization system (10) may be used intraoperatively to provide real-time, or near real-time, information to the clinician regarding proximity data, dimensions, and/or distances during a surgical procedure. The surgical visualization system (10) is configured for intraoperative identification of critical structure(s) and/or to facilitate the avoidance of critical structure(s) (11a, 11b) by a surgical device. For example, by identifying critical structures (11a, 11b), a clinician may avoid maneuvering a surgical device into a critical structure (11a, 11b) and/or a region in a predefined proximity of a critical structure (11a, 11b) during a surgical procedure. The clinician may avoid dissection of and/or near a vein, artery, nerve, and/or vessel, for example, identified as a critical structure (11a, 11b), for example. In various instances, critical structure(s) (11a, 11b) may be determined on a patient-by-patient and/or a procedure-by-procedure basis.

Critical structures (11a, 11b) may be any anatomical structures of interest. For example, a critical structure (11a, 11b) may be a ureter, an artery such as a superior mesenteric artery, a vein such as a portal vein, a nerve such as a phrenic nerve, and/or a sub-surface tumor or cyst, among other anatomical structures. In other instances, a critical structure (11a, 11b) may be any foreign structure in the anatomical field, such as a surgical device, surgical fastener, clip, tack, bougie, band, and/or plate, for example. In one aspect, a critical structure (11a, 11b) may be embedded in tissue. Stated differently, a critical structure (11a, 11b) may be positioned below a surface of the tissue. In such instances, the tissue conceals the critical structure (11a, 11b) from the clinician's view. A critical structure (11a, 11b) may also be obscured from the view of an imaging device by the tissue. The tissue may be fat, connective tissue, adhesions, and/or organs, for example. In other instances, a critical structure (11a, 11b) may be partially obscured from view. A surgical visualization system (10) is shown being utilized intraoperatively to identify and facilitate avoidance of certain critical structures, such as a ureter (11a) and vessels (11b) in an organ (12) (the uterus in this example), that are not visible on a surface (13) of the organ (12).

A. Overview of Exemplary Surgical Visualization System

With continuing reference to FIG. 1, the surgical visualization system (10) incorporates tissue identification and geometric surface mapping in combination with a distance sensor system (14). In combination, these features of the surgical visualization system (10) may determine a position of a critical structure (11a, 11b) within the anatomical field and/or the proximity of a surgical device (16) to the surface (13) of the visible tissue and/or to a critical structure (11a, 11b). The surgical device (16) may include an end effector having opposing jaws (not shown) and/or other structures extending from the distal end of the shaft of the surgical device (16). The surgical device (16) may be any suitable surgical device such as, for example, a dissector, a stapler, a grasper, a clip applier, a monopolar RF electrosurgical instrument, a bipolar RF electrosurgical instrument, and/or an ultrasonic instrument. As described herein, a surgical visualization system (10) may be configured to achieve identification of one or more critical structures (11a, 11b) and/or the proximity of a surgical device (16) to critical structure(s) (11a, 11b).

The depicted surgical visualization system (10) includes an imaging system that includes an imaging device (17), such as a camera or a scope, for example, that is configured to provide real-time views of the surgical site. In various instances, an imaging device (17) includes a spectral camera (e.g., a hyperspectral camera, multispectral camera, a fluorescence detecting camera, or selective spectral camera), which is configured to detect reflected or emitted spectral waveforms and generate a spectral cube of images based on the molecular response to the different wavelengths. Views from the imaging device (17) may be provided to a clinician; and, in various aspects of the present disclosure, may be augmented with additional information based on the tissue identification, landscape mapping, and input from a distance sensor system (14). In such instances, a surgical visualization system (10) includes a plurality of subsystems—an imaging subsystem, a surface mapping subsystem, a tissue identification subsystem, and/or a distance determining subsystem. These subsystems may cooperate to intraoperatively provide advanced data synthesis and integrated information to the clinician(s).

The imaging device (17) of the present example includes an emitter (18), which is configured to emit spectral light in a plurality of wavelengths to obtain a spectral image of hidden structures, for example. The imaging device (17) may also include a three-dimensional camera and associated electronic processing circuits in various instances. In one aspect, the emitter (18) is an optical waveform emitter that is configured to emit electromagnetic radiation (e.g., near-infrared radiation (NIR) photons) that may penetrate the surface (13) of a tissue (12) and reach critical structure(s) (11a, 11b). The imaging device (17) and optical waveform emitter (18) thereon may be positionable by a robotic arm or a surgeon manually operating the imaging device. A corresponding waveform sensor (e.g., an image sensor, spectrometer, or vibrational sensor, etc.) on the imaging device (17) may be configured to detect the effect of the electromagnetic radiation received by the waveform sensor.

The wavelengths of the electromagnetic radiation emitted by the optical waveform emitter (18) may be configured to enable the identification of the type of anatomical and/or physical structure, such as critical structure(s) (11a, 11b). The identification of critical structure(s) (11a, 11b) may be accomplished through spectral analysis, photo-acoustics, fluorescence detection, and/or ultrasound, for example. In one aspect, the wavelengths of the electromagnetic radiation may be variable. The waveform sensor and optical waveform emitter (18) may be inclusive of a multispectral imaging system and/or a selective spectral imaging system, for example. In other instances, the waveform sensor and optical waveform emitter (18) may be inclusive of a photoacoustic imaging system, for example. In other instances, an optical waveform emitter (18) may be positioned on a separate surgical device from the imaging device (17). By way of example only, the imaging device (17) may provide hyperspectral imaging in accordance with at least some of the teachings of U.S. Pat. No. 9,274,047, entitled "System and Method for Gross Anatomic Pathology Using Hyperspectral Imaging," issued Mar. 1, 2016, the disclosure of which is incorporated by reference herein in its entirety.

The depicted surgical visualization system (10) also includes an emitter (19), which is configured to emit a pattern of light, such as stripes, grid lines, and/or dots, to enable the determination of the topography or landscape of a surface (13). For example, projected light arrays may be used for three-dimensional scanning and registration on a surface (13). The projected light arrays may be emitted from an emitter (19) located on a surgical device (16) and/or an imaging device (17), for example. In one aspect, the projected light array is employed to determine the shape defined by the surface (13) of the tissue (12) and/or the motion of the surface (13) intraoperatively. An imaging device (17) is configured to detect the projected light arrays reflected from the surface (13) to determine the topography of the surface (13) and various distances with respect to the surface (13). By way of further example only, a visualization system (10) may utilize patterned light in accordance with at least some of the teachings of U.S. Pat. Pub. No. 2017/0055819, entitled "Set Comprising a Surgical Instrument," published Mar. 2, 2017, issued as U.S. Pat. No. 11,033,182 on Jun. 15, 2021, the disclosure of which is incorporated by reference herein in its entirety; and/or U.S. Pat. Pub. No. 2017/0251900, entitled "Depiction System," published Sep. 7, 2017, issued as U.S. Pat. No. 11,039,734 on Jun. 22, 2021, the disclosure of which is incorporated by reference herein in its entirety.

The depicted surgical visualization system (10) also includes a distance sensor system (14) configured to determine one or more distances at the surgical site. In one aspect, the distance sensor system (14) may include a time-of-flight distance sensor system that includes an emitter, such as the structured light emitter (19); and a receiver (not shown), which may be positioned on the surgical device (16). In other instances, the time-of-flight emitter may be separate from the structured light emitter. In one general aspect, the emitter portion of the time-of-flight distance sensor system (14) may include a laser source and the receiver portion of the time-of-flight distance sensor system (14) may include a matching sensor. A time-of-flight distance sensor system (14) may detect the "time of flight," or how long the laser light emitted by the structured light emitter (19) has taken to bounce back to the sensor portion of the receiver. Use of a very narrow light source in a structured light emitter (19) may enable a distance sensor system (14) to determine the distance to the surface (13) of the tissue (12) directly in front of the distance sensor system (14).

Referring still to FIG. 1, a distance sensor system (14) may be employed to determine an emitter-to-tissue distance ($d_e$) from a structured light emitter (19) to the surface (13) of the tissue (12). A device-to-tissue distance ($d_t$) from the distal end of the surgical device (16) to the surface (13) of the tissue (12) may be obtainable from the known position of the emitter (19) on the shaft of the surgical device (16) relative to the distal end of the surgical device (16). In other words, when the distance between the emitter (19) and the distal end of the surgical device (16) is known, the device-to-tissue distance ($d_t$) may be determined from the emitter-to-tissue distance ($d_e$). In certain instances, the shaft of a surgical device (16) may include one or more articulation joints; and may be articulatable with respect to the emitter (19) and the jaws. The articulation configuration may include a multi-joint vertebrae-like structure, for example. In certain instances, a three-dimensional camera may be utilized to triangulate one or more distances to the surface (13).

As described above, a surgical visualization system (10) may be configured to determine the emitter-to-tissue distance ($d_e$) from an emitter (19) on a surgical device (16) to the surface (13) of a uterus (12) via structured light. The surgical visualization system (10) is configured to extrapolate a device-to-tissue distance ($d_t$) from the surgical device (16) to the surface (13) of the uterus (12) based on emitter-to-tissue distance ($d_e$). The surgical visualization system (10) is also configured to determine a tissue-to-ureter distance ($d_A$) from a ureter (11a) to the surface (13) and a camera-to-ureter distance ($d_w$), from the imaging device (17) to the ureter (11a). Surgical visualization system (10) may determine the camera-to-ureter distance ($d_w$), with spectral imaging and time-of-flight sensors, for example. In various instances, a surgical visualization system (10) may determine (e.g., triangulate) a tissue-to-ureter distance ($d_A$) (or depth) based on other distances and/or the surface mapping logic described herein.

B. First Exemplary Control System

Figure 2:
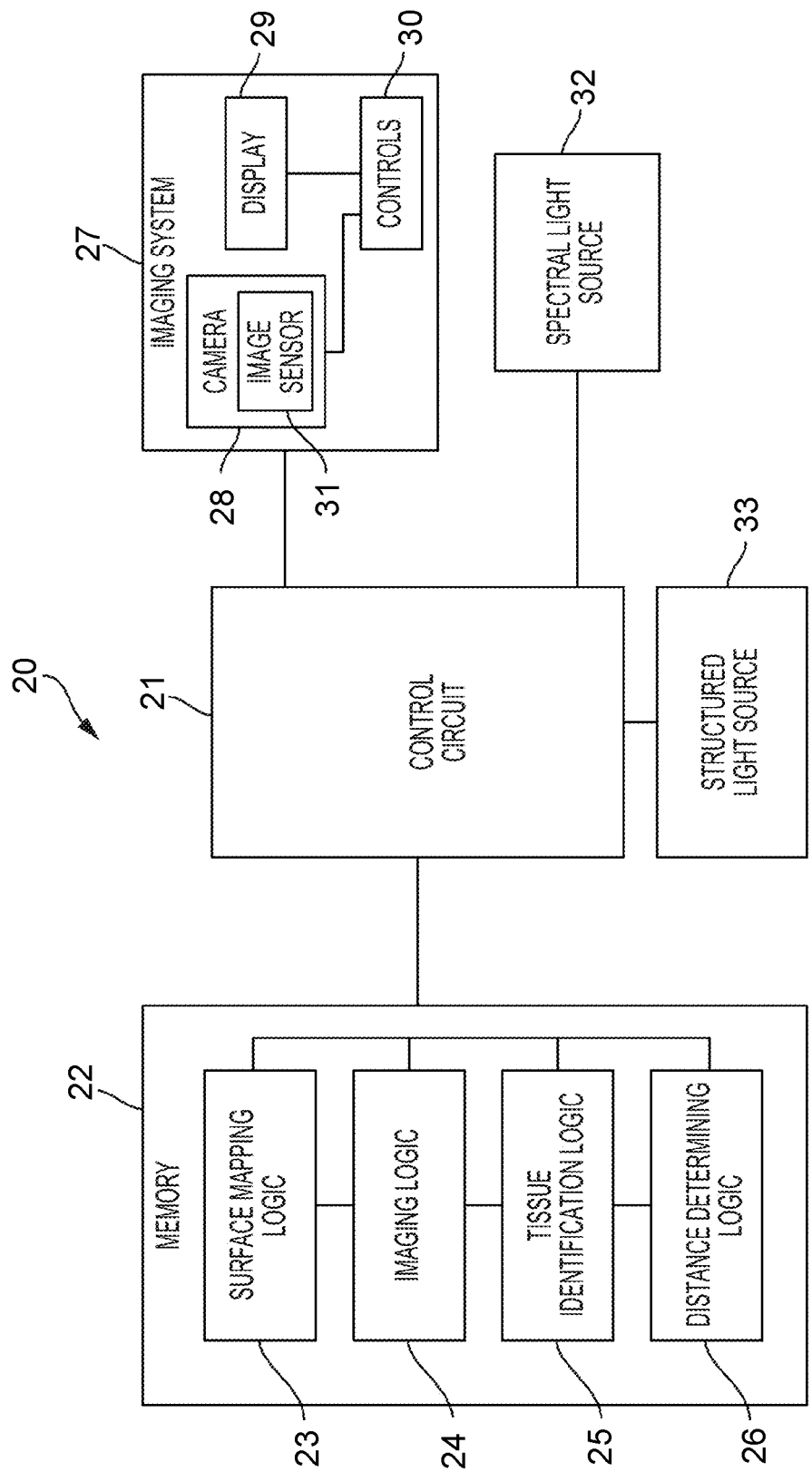
FIG. 2 depicts a schematic diagram of an exemplary control system that may be used with the surgical visualization system of FIG. 1.

FIG. 2 is a schematic diagram of a control system (20), which may be utilized with a surgical visualization system (10). The depicted control system (20) includes a control circuit (21) in signal communication with a memory (22). The memory (22) stores instructions executable by the control circuit (21) to determine and/or recognize critical structures (e.g., critical structures (11a, 11b) depicted in FIG. 1), determine and/or compute one or more distances and/or three-dimensional digital representations, and to communicate certain information to one or more clinicians. For example, a memory (22) stores surface mapping logic (23), imaging logic (24), tissue identification logic (25), or distance determining logic (26) or any combinations of logic (23, 24, 25, 26). The control system (20) also includes an imaging system (27) having one or more cameras (28) (like the imaging device (17) depicted in FIG. 1), one or more displays (29), one or more controls (30) or any combinations of these elements. The one or more cameras (28) may include one or more image sensors (31) to receive signals from various light sources emitting light at various visible and invisible spectra (e.g., visible light, spectral imagers, three-dimensional lens, among others). The display (29) may include one or more screens or monitors for depicting real, virtual, and/or virtually-augmented images and/or information to one or more clinicians.

In various aspects, a main component of a camera (28) includes an image sensor (31). An image sensor (31) may include a Charge-Coupled Device (CCD) sensor, a Complementary Metal Oxide Semiconductor (CMOS) sensor, a short-wave infrared (SWIR) sensor, a hybrid CCD/CMOS architecture (sCMOS) sensor, and/or any other suitable kind(s) of technology. An image sensor (31) may also include any suitable number of chips.

The depicted control system (20) also includes a spectral light source (32) and a structured light source (33). In certain instances, a single source may be pulsed to emit wavelengths of light in the spectral light source (32) range and wavelengths of light in the structured light source (33) range. Alternatively, a single light source may be pulsed to provide light in the invisible spectrum (e.g., infrared spectral light) and wavelengths of light on the visible spectrum. A spectral light source (32) may include a hyperspectral light source, a multispectral light source, a fluorescence excitation light source, and/or a selective spectral light source, for example. In various instances, tissue identification logic (25) may identify critical structure(s) via data from a spectral light source (32) received by the image sensor (31) portion of a camera (28). Surface mapping logic (23) may determine the surface contours of the visible tissue based on reflected structured light. With time-of-flight measurements, distance determining logic (26) may determine one or more di stance(s) to the visible tissue and/or critical structure(s) (11a, 11b). One or more outputs from surface mapping logic (23), tissue identification logic (25), and distance determining logic (26), may be provided to imaging logic (24), and combined, blended, and/or overlaid to be conveyed to a clinician via the display (29) of the imaging system (27).

C. Second Exemplary Control System

Figure 3:
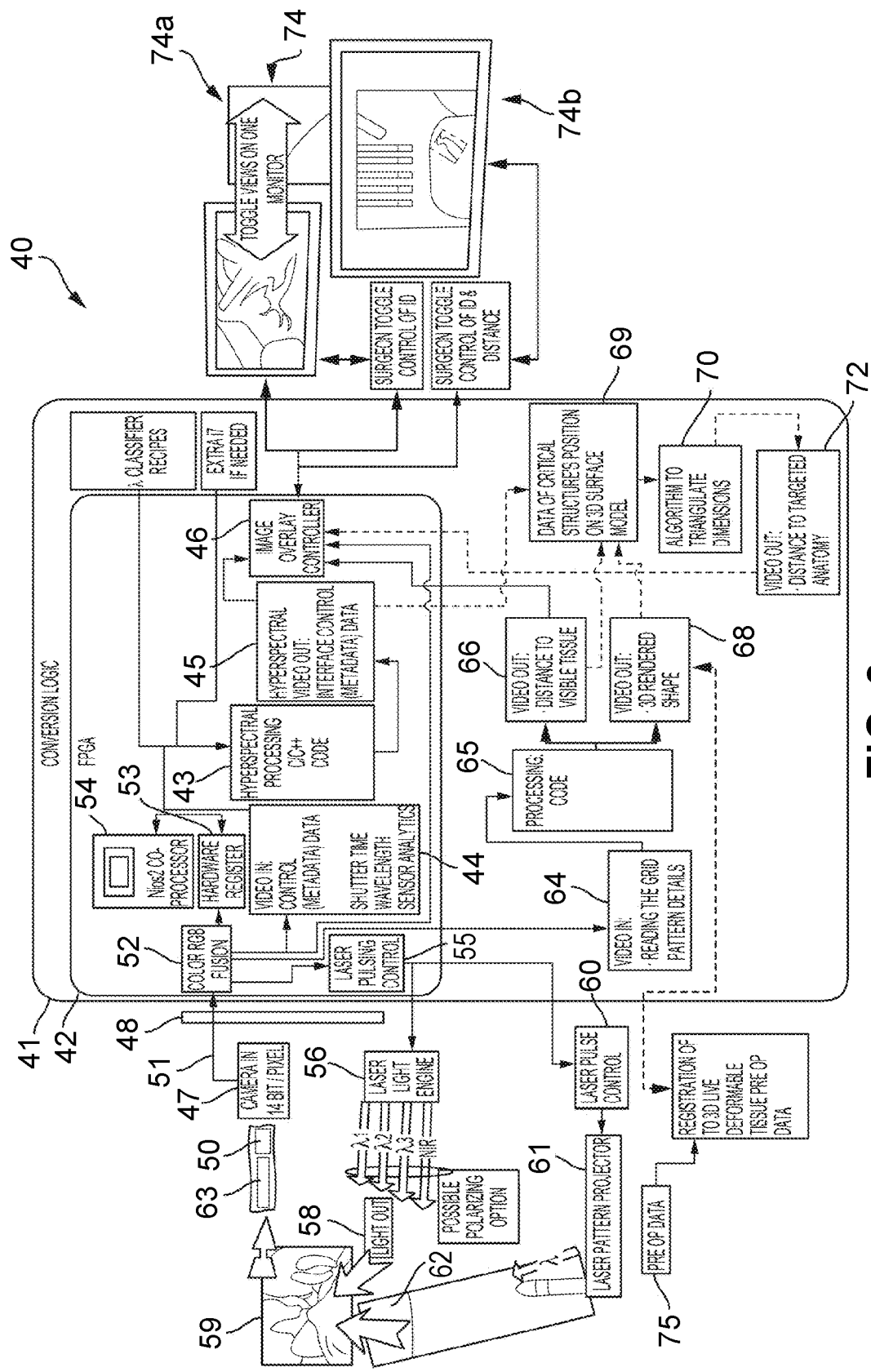
FIG. 3 depicts a schematic diagram of another exemplary control system that may be used with the surgical visualization system of FIG. 1.

FIG. 3 depicts a schematic of another control system (40) for a surgical visualization system, such as the surgical visualization system (10) depicted in FIG. 1, for example. This control system (40) is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system (40) depicted in FIG. 3 is configured for implementing a hyperspectral or fluorescence imaging and visualization system in which a molecular response is utilized to detect and identify anatomy in a surgical field of view. This control system (40) includes a conversion logic circuit (41) to convert tissue data to surgeon usable information. For example, the variable reflectance based on wavelengths with respect to obscuring material may be utilized to identify a critical structure in the anatomy. Moreover, this control system (40) combines the identified spectral signature and the structured light data in an image. For example, this control system (40) may be employed to create a three-dimensional data set for surgical use in a system with augmentation image overlays. Techniques may be employed both intraoperatively and preoperatively using additional visual information. In various instances, this control system (40) is configured to provide warnings to a clinician when in the proximity of one or more critical structures. Various algorithms may be employed to guide robotic automation and semi-automated approaches based on the surgical procedure and proximity to the critical structure(s).

The control system (40) depicted in FIG. 3 is configured to detect the critical structure(s) and provide an image overlay of the critical structure and measure the distance to the surface of the visible tissue and the distance to the embedded/buried critical structure(s). In other instances, this control system (40) may measure the distance to the surface of the visible tissue or detect the critical structure(s) and provide an image overlay of the critical structure.

The control system (40) depicted in FIG. 3 includes a spectral control circuit (42). The spectral control circuit (42) includes a processor (43) to receive video input signals from a video input processor (44). The processor (43) is configured to process the video input signal from the video input processor (44) and provide a video output signal to a video output processor (45), which includes a hyperspectral video-out of interface control (metadata) data, for example. The video output processor (45) provides the video output signal to an image overlay controller (46).

The video input processor (44) is coupled to a camera (47) at the patient side via a patient isolation circuit (48). As previously discussed, the camera (47) includes a solid state image sensor (50). The camera (47) receives intraoperative images through optics (63) and the image sensor (50). An isolated camera output signal (51) is provided to a color RGB fusion circuit (52), which employs a hardware register (53) and a Nios2 co-processor (54) to process the camera output signal (51). A color RGB fusion output signal is provided to the video input processor (44) and a laser pulsing control circuit (55).

The laser pulsing control circuit (55) controls a light engine (56). In some versions, light engine (56) includes any one or more of lasers, LEDs, incandescent sources, and/or interface electronics configured to illuminate the patient's body habitus with a chosen light source for imaging by a camera and/or analysis by a processor. The light engine (56) outputs light in a plurality of wavelengths ($\lambda 1, \lambda 2, \lambda 3 \ldots \lambda n$) including near infrared (NIR) and broadband white light. The light output (58) from the light engine (56) illuminates targeted anatomy in an intraoperative surgical site (59). The laser pulsing control circuit (55) also controls a laser pulse controller (60) for a laser pattern projector (61) that projects a laser light pattern (62), such as a grid or pattern of lines and/or dots, at a predetermined wavelength ($\lambda 2$) on the operative tissue or organ at the surgical site (59). the camera (47) receives the patterned light as well as the reflected or emitted light output through camera optics (63). The image sensor (50) converts the received light into a digital signal.

The color RGB fusion circuit (52) also outputs signals to the image overlay controller (46) and a video input module (64) for reading the laser light pattern (62) projected onto the targeted anatomy at the surgical site (59) by the laser pattern projector (61). A processing module (65) processes the laser light pattern (62) and outputs a first video output signal (66) representative of the distance to the visible tissue at the surgical site (59). The data is provided to the image overlay controller (46). The processing module (65) also outputs a second video signal (68) representative of a three-dimensional rendered shape of the tissue or organ of the targeted anatomy at the surgical site.

The first and second video output signals (66, 68) include data representative of the position of the critical structure on a three-dimensional surface model, which is provided to an integration module (69). In combination with data from the video output processor (45) of the spectral control circuit (42), the integration module (69) may determine distance ($d_A$) (FIG. 1) to a buried critical structure (e.g., via triangularization algorithms (70)), and that distance ($d_A$) may be provided to the image overlay controller (46) via a video out processor (72). The foregoing conversion logic may encompass a conversion logic circuit (41), intermediate video monitors (74), and a camera (56)/laser pattern projector (61) positioned at surgical site (59).

Preoperative data (75) from a CT or MRI scan may be employed to register or align certain three-dimensional deformable tissue in various instances. Such preoperative data (75) may be provided to an integration module (69) and ultimately to the image overlay controller (46) so that such information may be overlaid with the views from the camera (47) and provided to video monitors (74). Registration of preoperative data is further described herein and in U.S. Pat. Pub. No. 2020/0015907, entitled "Integration of Imaging Data," published Jan. 16, 2020, for example, which is incorporated by reference herein in its entirety.

Video monitors (74) may output the integrated/augmented views from the image overlay controller (46). On a first monitor (74a), the clinician may toggle between (A) a view in which a three-dimensional rendering of the visible tissue is depicted and (B) an augmented view in which one or more hidden critical structures are depicted over the three-dimensional rendering of the visible tissue. On a second monitor (74b), the clinician may toggle on distance measurements to one or more hidden critical structures and/or the surface of visible tissue, for example.

D. Exemplary Hyperspectral Identifying Signatures

Figure 4:
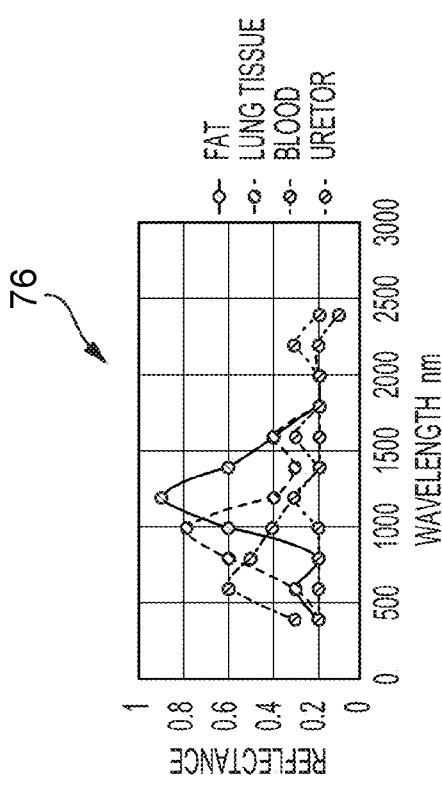
FIG. 4 depicts exemplary hyperspectral identifying signatures to differentiate anatomy from obscurants, and more particularly depicts a graphical representation of a ureter signature versus obscurants.
Figure 6:
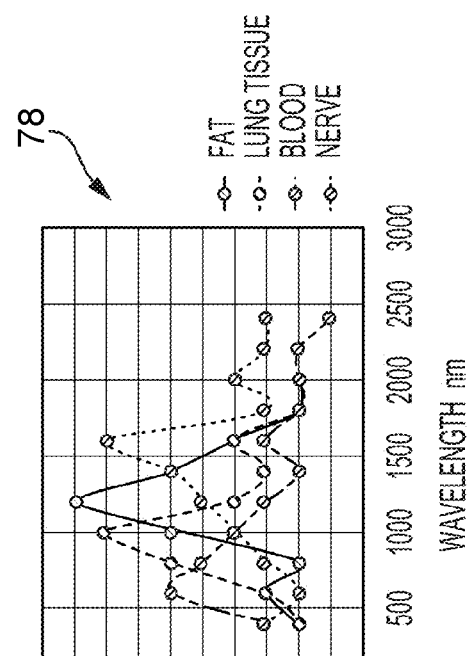
FIG. 6 depicts exemplary hyperspectral identifying signatures to differentiate anatomy from obscurants, and more particularly depicts a graphical representation of a nerve signature versus obscurants.
Figure 5:
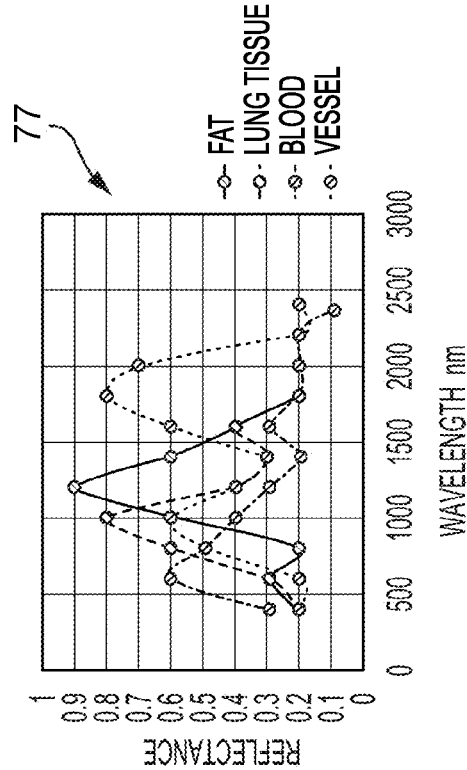
FIG. 5 depicts exemplary hyperspectral identifying signatures to differentiate anatomy from obscurants, and more particularly depicts a graphical representation of an artery signature versus obscurants.

FIG. 4 depicts a graphical representation (76) of an illustrative ureter signature versus obscurants. The plots represent reflectance as a function of wavelength (nm) for wavelengths for fat, lung tissue, blood, and a ureter. FIG. 5 depicts a graphical representation (77) of an illustrative artery signature versus obscurants. The plots represent reflectance as a function of wavelength (nm) for fat, lung tissue, blood, and a vessel. FIG. 6 depicts a graphical representation (78) of an illustrative nerve signature versus obscurants. The plots represent reflectance as a function of wavelength (nm) for fat, lung tissue, blood, and a nerve.

In various instances, select wavelengths for spectral imaging may be identified and utilized based on the anticipated critical structures and/or obscurants at a surgical site (i.e., "selective spectral" imaging). By utilizing selective spectral imaging, the amount of time required to obtain the spectral image may be minimized such that the information may be obtained in real-time, or near real-time, and utilized intraoperatively. In various instances, the wavelengths may be selected by a clinician or by a control circuit based on input by the clinician. In certain instances, the wavelengths may be selected based on machine learning and/or big data accessible to the control circuit via a cloud, for example.

E. Exemplary Singular EMR Source Emitter Assembly

Figure 7A:
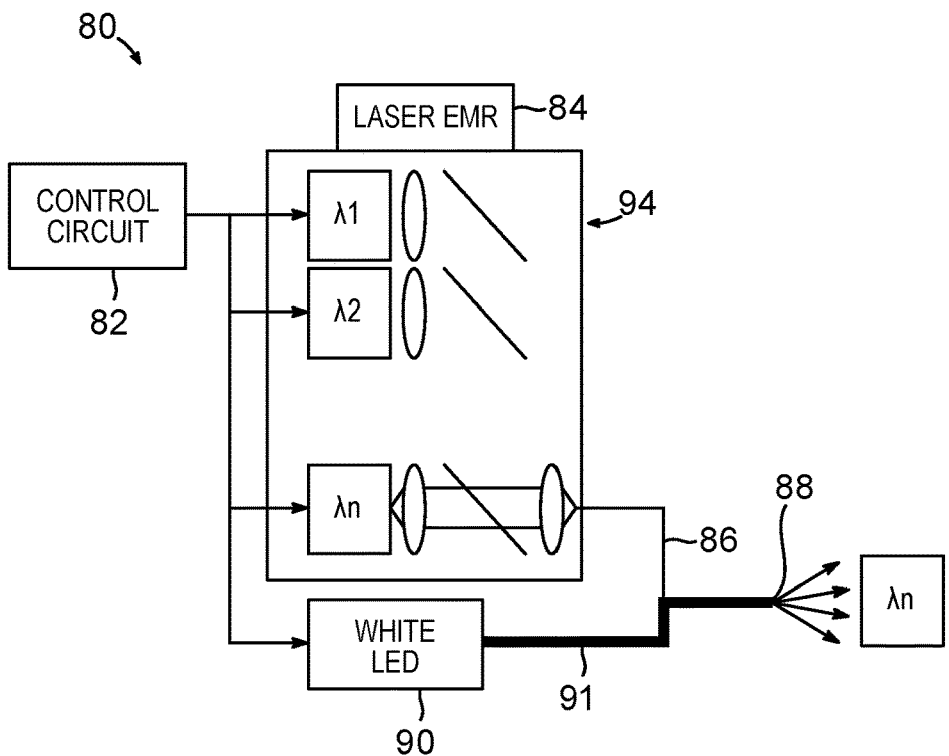
FIG. 7A depicts a schematic view of an exemplary emitter assembly that may be incorporated into the surgical visualization system of FIG. 1, the emitter assembly including a single electromagnetic radiation (EMR) source, showing the emitter assembly in a first state.
Figure 7B:
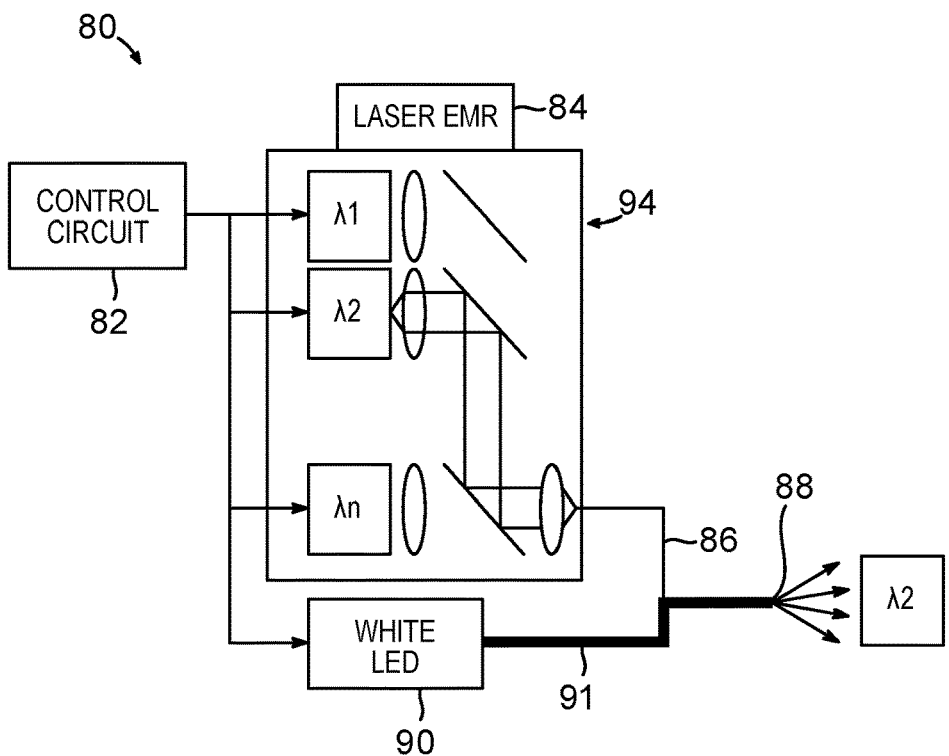
FIG. 7B depicts a schematic view of the emitter assembly of FIG. 7A, showing the emitter assembly in a second state.
Figure 7C:
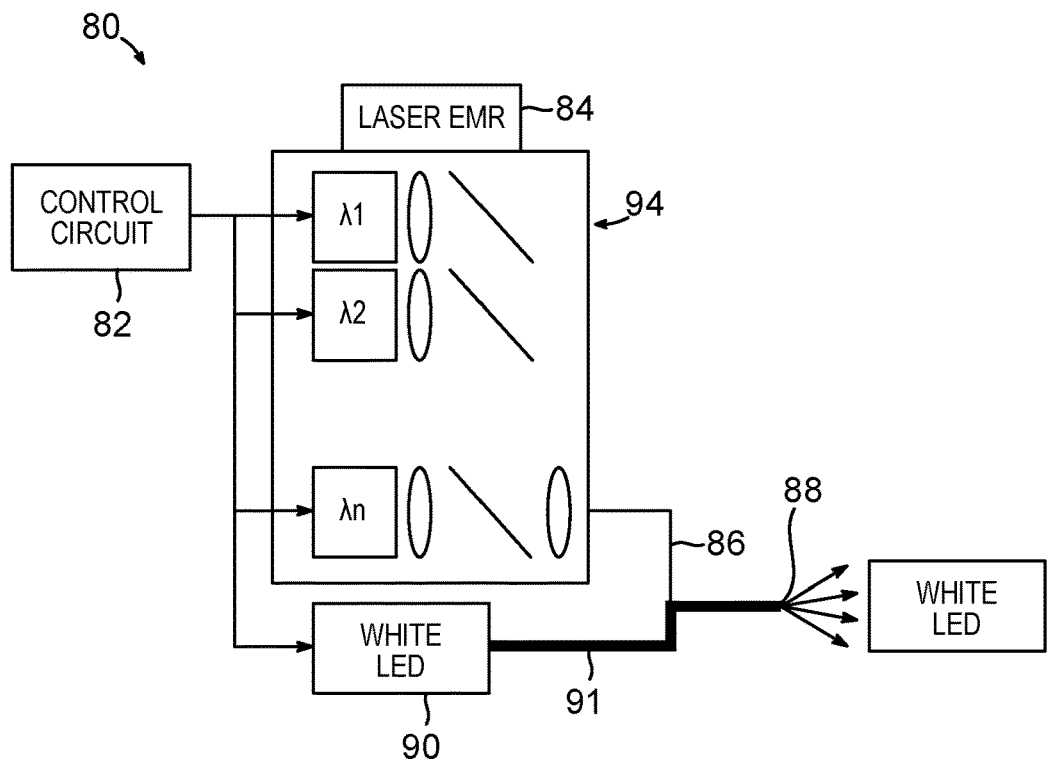
FIG. 7C depicts a schematic view of the emitter assembly of FIG. 7A, showing the emitter assembly in a third state.

Referring now to FIGS. 7A-7C, in one aspect, a visualization system (10) includes a receiver assembly (e.g., positioned on a surgical device (16)), which may include a camera (47) including an image sensor (50) (FIG. 3), and an emitter assembly (80) (e.g., positioned on imaging device (17)), which may include an emitter (18) (FIG. 1) and/or a light engine (56) (FIG. 3). Further, a visualization system (10) may include a control circuit (82), which may include the control circuit (21) depicted in FIG. 2 and/or the spectral control circuit (42) depicted in FIG. 3, coupled to each of emitter assembly (80) and the receiver assembly. An emitter assembly (80) may be configured to emit EMR at a variety of wavelengths (e.g., in the visible spectrum and/or in the IR spectrum) and/or as structured light (i.e., EMR projected in a particular known pattern). A control circuit (82) may include, for example, hardwired circuitry, programmable circuitry (e.g., a computer processor coupled to a memory or field programmable gate array), state machine circuitry, firmware storing instructions executed by programmable circuitry, and any combination thereof.

In one aspect, an emitter assembly (80) may be configured to emit visible light, IR, and/or structured light from a single EMR source (84). For example, FIGS. 7A-7C illustrate a diagram of an emitter assembly (80) in alternative states, in accordance with at least one aspect of the present disclosure. In this aspect, an emitter assembly (80) comprises a channel (86) connecting an EMR source (84) to an emitter (88) configured to emit visible light (e.g., RGB), IR, and/or structured light in response to being supplied EMR of particular wavelengths from the EMR source (84). The channel (86) may include, for example, a fiber optic cable. The EMR source (84) may include, for example, a light engine (56) (FIG. 3) including a plurality of light sources configured to selectively output light at respective wavelengths. In the example shown, the emitter assembly (80) also comprises a white LED (90) connected to the emitter (88) via another channel (91).

The depicted emitter assembly (80) further includes a wavelength selector assembly (94) configured to direct EMR emitted from the light sources of the EMR source (84) toward the first emitter (88). In the depicted aspect, the wavelength selector assembly (94) includes a plurality of deflectors and/or reflectors configured to transmit EMR from the light sources of the EMR source (84) to the emitter (88).

In one aspect, a control circuit (82) may be electrically coupled to each light source of the EMR source (84) such that it may control the light outputted therefrom via applying voltages or control signals thereto. The control circuit (82) may be configured to control the light sources of the EMR source (84) to direct EMR from the EMR source (84) to the emitter (88) in response to, for example, user input and/or detected parameters (e.g., parameters associated with the surgical instrument or the surgical site). In one aspect, the control circuit (82) is coupled to the EMR source (84) such that it may control the wavelength of the EMR generated by the EMR source (84). In various aspects, the control circuit (82) may control the light sources of the EMR source (84) either independently or in tandem with each other.

In some aspects, the control circuit (82) may adjust the wavelength of the EMR generated by the EMR source (84) according to which light sources of the EMR source (84) are activated. In other words, the control circuit (82) may control the EMR source (84) so that it produces EMR at a particular wavelength or within a particular wavelength range. For example, in FIG. 7A, the control circuit (82) has applied control signals to the nth light source of the EMR source (84) to cause it to emit EMR at an nth wavelength ($\lambda n$), and has applied control signals to the remaining light sources of the EMR source (84) to prevent them from emitting EMR at their respective wavelengths. Conversely, in FIG. 7B the control circuit (82) has applied control signals to the second light source of the EMR source (84) to cause it to emit EMR at a second wavelength ($\lambda 2$), and has applied control signals to the remaining light sources of the EMR source (84) to prevent them from emitting EMR at their respective wavelengths. Furthermore, in FIG. 7C the control circuit (82) has applied control signals to the light sources of the EMR source (84) to prevent them from emitting EMR at their respective wavelengths, and has applied control signals to a white LED source to cause it to emit white light.

In addition to the foregoing, at least part of any one or more of the surgical visualization system (10) depicted in FIG. 1, the control system (20) depicted in FIG. 2, the control system (40) depicted in FIG. 3, and/or the emitter assembly (80) depicted in FIGS. 7A and 7B may be configured and operable in accordance with at least some of the teachings of U.S. Pat. Pub. No. 2020/0015925, entitled "Combination Emitter and Camera Assembly," published Jan. 16, 2020, issued as U.S. Pat. No. 11,754,712 on Sep. 12, 2023, which is incorporated by reference above. In one aspect, a surgical visualization system (10) may be incorporated into a robotic system in accordance with at least some of such teachings.

Figure 8A:
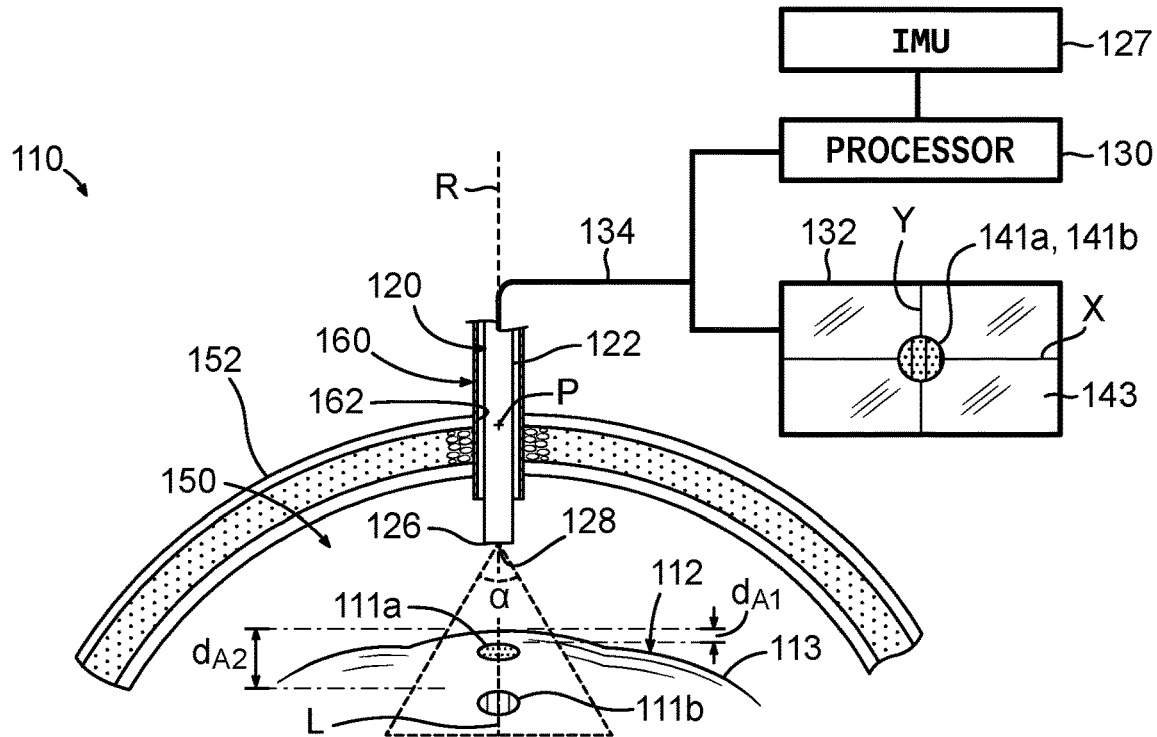
FIG. 8A depicts a schematic view of another exemplary surgical visualization system including an imaging device and a display, showing the imaging device aiming directly at a pair of aligned nodules below a tissue surface, and further showing the display presenting overlapped visual representations of both nodules at an origin of a 2-dimensional coordinate system defined by the imaging device's line of sight.
Figure 8B:
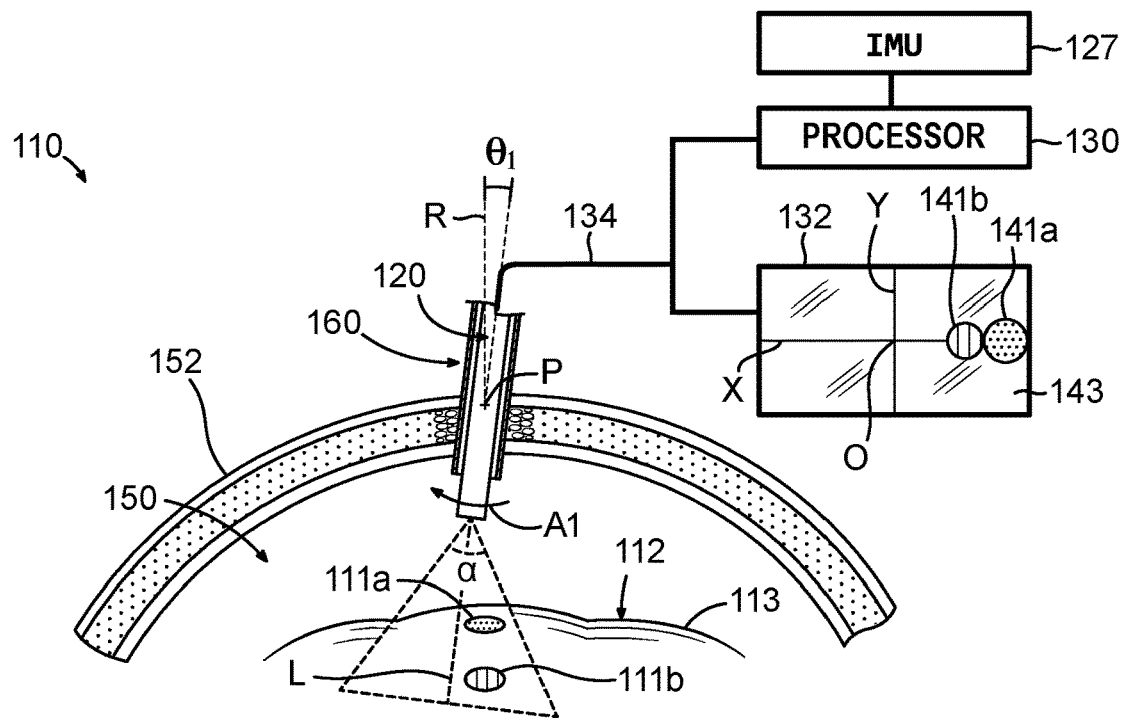
FIG. 8B depicts a schematic view of the surgical visualization system of FIG. 8A, showing the imaging device pivoted clockwise about its insertion point to sweep leftward over the pair of aligned nodules, and further showing the display presenting offset visual representations of the nodules translated rightward along a first axis of the coordinate system.
Figure 8C:
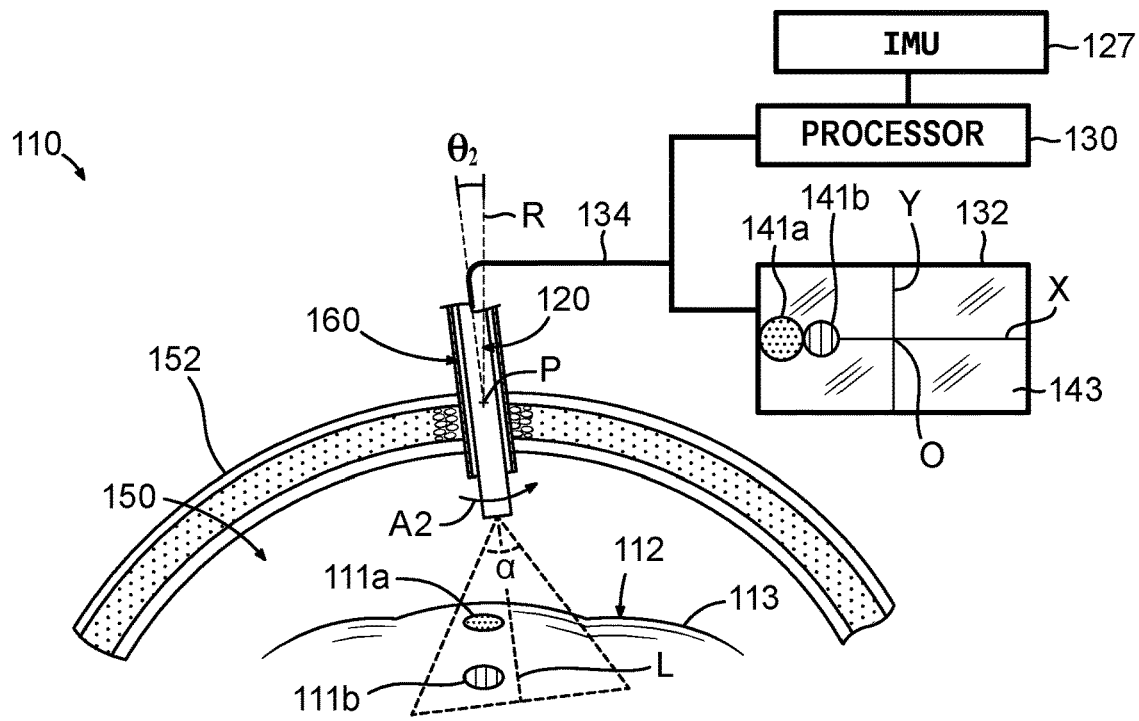
FIG. 8C depicts a schematic view of the surgical visualization system of FIG. 8A, showing the imaging device pivoted counterclockwise about its insertion point to sweep rightward over the pair of aligned nodules, and further showing the display presenting offset visual representations of the nodules translated leftward along the first axis.

II. Exemplary Surgical Visualization System with Critical Structure Depth Estimation In some instances, it may be desirable to provide a surgical visualization system that is configured to determine a depth of one or more critical structures (11a, 11b) below a surface (13) of tissue (12), such as tissue-to-ureter distance ($d_A$), in a manner different from that described above. FIGS. 8A-8C depict a surgical visualization system (110) which provides such functionality. Surgical visualization system (110) is shown being utilized intraoperatively to identify certain critical structures such as first and second nodules (111a, 111b) in an organ such as a lung (112) that are each embedded below a surface (113) of lung (112), and to determine the respective depths ($d_{41}$, $d_{42}$) of such nodules (111a, 111b) below surface (113). Surgical visualization system (110) is similar to surgical visualization system (10) described above except as otherwise described below.

Surgical visualization system (110) of this example comprises an imaging device in the form of an endoscope (120) that is configured to provide real-time views of a surgical site. Endoscope (120) includes an elongate shaft (122), which extends distally from a handle (not shown) to a distal end (126). In some versions, endoscope (120) may include an inertial measurement unit (IMU) (127), such as within the handle of endoscope (120), for measuring an orientation of endoscope (120) relative to a reference axis (R), as described in greater detail below. Endoscope (120) also includes a spectral camera (128), which is positioned at distal end (126) and configured to detect reflected spectral waveforms and generate a spectral cube of images based on the molecular response to the different wavelengths in a manner similar to that described above with regard to imaging device (17). As shown, camera (128) defines an angle of view ($\alpha$) and a line of sight (L), which in the present version is coaxial with shaft (122). In some versions, line of sight (L) may be offset from the axis of shaft (122) by an angle, such as approximately 30°.

Surgical visualization system (110) of this example further comprises a processor (130) in operative communication with each of endoscope (120) and a display (132) via one or more cables (134). Display (132) may include one or more screens or monitors for depicting real, virtual, and/or virtually-augmented images and/or information to one or more clinicians in a manner similar to that described above with regard to display (29). In this manner, views from endoscope (120) may be communicated to display (132) via cable (134) and thereby conveyed to a clinician. As shown in FIGS. 8A-8C, each of these views presented by display (132) may include visual representations of any one or more anatomical structures captured within angle of view ($\alpha$), such as first and second nodule representations (141a, 141b) and a lung surface representation (143). In the present version, display (132) augments the depicted representations in each view with a 2-dimensional coordinate system having first and second axes (X, Y) and defined by camera (128). For example, such a coordinate system may be arranged perpendicular to line of sight (L) of camera (128) with line of sight (L) extending through and thereby defining an origin (O) of the coordinate system.

It will be appreciated that nodule representations (141a, 141b) and lung surface representation (143) may be acquired by camera (128) and communicated to processor (130) and/or display (132) using any suitable techniques, such as via multispectral or fluorescence imaging as described above. In some versions, one or more fluorescent agents may be delivered to lung (112) and/or one or both nodules (111a, 111b) to assist with facilitating the acquisition of any one or more of representations (141a, 141b, 143), for example. In addition or alternatively, processor (130) may be in operative communication with one or both of endoscope (130) and/or display (132) via a suitable wireless communication protocol.

With continuing reference to FIGS. 8A-8C, at least a distal portion of endoscope (120) is inserted into a thoracic cavity (150) of a patient through the patient's thoracic wall (152) to allow camera (128) to visualize lung (112) and thereby allow display (132) to present lung surface representation (143). In the present version, endoscope (120) accesses thoracic cavity (150) via a trocar (160). More particularly, the distal portion of endoscope (120) is received distally through a working channel (162) of trocar (160). In this regard, shaft (122) may have a cross sectional dimension slightly less than that of working channel (162) such that shaft (122) may be slidably received therein. Shaft (122) and/or line of sight (L) of endoscope (120) may be selectively pivoted together with trocar (160) about the insertion point (P) of trocar (160) at the patient's thoracic wall (152), as described in greater detail below. In this regard, reference axis (R) may be used for measuring one or more orientations of endoscope (120) about insertion point (P). Reference axis (R) may be defined in any suitable manner. For example, reference axis (R) may be a vertical axis and/or an axis that line of sight (L) extends along when aimed directly at one or both nodules (111a, 111b).

As shown in FIG. 8A, endoscope (120) and line of sight (L) are each oriented about insertion point (P) coaxially with reference axis (R) and aimed directly at first and second nodules (111a, 111b) embedded below surface (113) of lung (112). More particularly, first and second nodules (111a, 111b) are each captured within angle of view ($\alpha$) and centered therein along line of sight (L), such that first and second nodules (111a, 111b) are aligned with each other along line of sight (L). Due to this alignment of first and second nodules (111a, 111b) along line of sight (L), display (132) presents the respective nodule representations (141a, 141b) overlapping with each other at the origin (O) of the coordinate system, i.e., at the intersection of the first and second axes (X, Y).

In the present version, endoscope (120) is pivotable in a clockwise direction about insertion point (P) to transition line of sight (L) from the orientation shown in FIG. 8A to the orientation shown in FIG. 8B, as indicated by arrow (A1) in FIG. 8B.

As shown in FIG. 8B, endoscope (120) and line of sight (L) are each oriented about insertion point (P) at a first sweep angle ($\theta_1$) relative to reference axis (R) and aimed slightly left of first and second nodules (111a, 111b). More particularly, first and second nodules (111a, 111b) each remain captured within angle of view ($\alpha$) and are positioned to the right of line of sight (L), such that line of sight (L) is leftward of first and second nodules (111a, 111b). Due to this positioning of first and second nodules (111a, 111b) to the right of line of sight (L), display (132) presents the respective nodule representations (141a, 141b) translated to the right of the origin (O) of the coordinate system and offset from each other along the first axis (X). In this regard, since first nodule (111a) is closer to surface (113) of lung (112) than second nodule (111b), and thus closer to camera (128) than second nodule (111b), first nodule representation (141a) is translated further rightward from the origin (O) than second nodule representation (141b). Display (132) likewise presents lung surface representation (143) translated rightwardly relative to its position in FIG. 8A. In the present version, endoscope (120) is pivotable in a counter-clockwise direction about insertion point (P) to transition line of sight (L) from the orientation shown in FIG. 8B to the orientation shown in FIG. 8C, as indicated by arrow (A2) in FIG. 8C.

As shown in FIG. 8C, endoscope (120) and line of sight (L) are each oriented about insertion point (P) at a second sweep angle ($\theta_2$) relative to reference axis (R) and aimed slightly right of first and second nodules (111a, 111b). More particularly, first and second nodules (111a, 111b) each remain captured within angle of view ($\alpha$) and are positioned to the left of line of sight (L), such that line of sight (L) is rightward of first and second nodules (111a, 111b). Due to this positioning of first and second nodules (111a, 111b) to the left of line of sight (L), display (132) presents the respective nodule representations (141a, 141b) translated to the left of the origin (O) of the coordinate system and offset from each other along the first axis (X). In this regard, since first nodule (111a) is closer to surface (113) of lung (112) than second nodule (111b), and thus closer to camera (128) than second nodule (111b), first nodule representation (141a) is translated further leftward from the origin (O) than second nodule representation (141b). Display (132) likewise presents lung surface representation (143) translated leftwardly relative to its positions in FIGS. 8A and 8B.

It will be appreciated that the invention is not limited to scenarios having first and second nodules (111a, 111b) but instead is applicable to scenarios in which a single nodule (111a, 111b) or any other number of nodules (111a, 111b) is present. In this regard, the first and second nodules (111a, 111b) shown in the present version illustrate the differing apparent motion of a relatively shallow nodule (111a) and a relatively deep nodule (111b). As evident from a visual comparison of FIGS. 8A-8C, if an identified nodule is relatively shallow beneath surface (113) of lung (112), such as first nodule (111a), then the relative motion of the respective nodule representation, such as first nodule representation (141a) may be very similar to the relative motion of lung surface representation (143). On the other hand, if an identified nodule is relatively deep beneath surface (113) of lung (112), such as second nodule (111b), then the relative motion of the respective nodule representation, such as second nodule representation (141b) may be substantially slower than the relative motion of lung surface representation (143). As described in greater detail below, the difference in relative motion of surface (113) of lung (112) and the center of the projected area of the identified nodule (111a, 111b) is correlated to the depth of the identified nodule (111a, 111b) under surface (113) of lung (112).

The magnitudes of sweep angles ($\theta_1$, $\theta_2$) may collectively define a total sweep angle through which line of sight (L) is pivoted from the orientation shown in FIG. 8B to the orientation shown in FIG. 8C. In some versions, second sweep angle ($\theta_2$) may have a magnitude substantially equal to that of first sweep angle ($\theta_1$) and/or may have a sign opposite to that of first sweep angle ($\theta_1$). For example, first sweep angle ($\theta_1$) may have a positive value and second sweep angle ($\theta_2$) may have an equal and opposite negative value, such that the total sweep angle may have a magnitude substantially twice that of either sweep angle ($\theta_1$, $\theta_2$).

It will be appreciated that the movement of nodule representations (141a, 141b) and of lung surface representation (143) along the first and/or second axes (X, Y) as presented by display (132) during pivoting of line of sight (L) about insertion point (P) relative to reference axis (R) is indicative of the apparent motion of the respective nodules (111a, 111b) and lung surface (113) as perceived by endoscope (120). In other words, the movement of nodule representations (141a, 141b) and of lung surface representation (143) presented by display (132) indicates the relative motion between endoscope (120) and the respective nodules (111a, 111b) and lung surface (113). Such relative motion may differ for each of nodules (111a, 111b) and lung surface (113). For example, during pivoting of line of sight (L) from the orientation shown in FIG. 8A to the orientation shown in FIG. 8B, second nodule representation (141b) may translate rightwardly at a slower rate than that of first nodule representation (141a), and first nodule representation (141a) may likewise translate rightwardly at a slower rate than that of lung surface representation (143) but faster than that of second nodule representation (141b). Similarly, during pivoting of line of sight (L) from the orientation shown in FIG. 8B to the orientation shown in FIG. 8C, second nodule representation (141b) may translate leftwardly at a slower rate than that of first nodule representation (141a), and first nodule representation (141a) may likewise translate leftwardly at a slower rate than that of lung surface representation (143) but faster than that of second nodule representation (141b). The difference between nodule translation rate and tissue surface translation rate may be correlated to the depth of the center of mass of the respective nodule (111a, 111b).

As described in greater detail below, processor (130) of the present example is configured to monitor various sweep parameters associated with the pivoting of line of sight (L) and to determine the depth(s) ($d_{A1}$, $d_{A2}$) of one or more nodules (111a, 111b) below the tissue surface (113) based on the monitored sweep parameters. Such sweep parameters may include: the differences in apparent motion between that of lung surface (113) and one or more nodules (111a, 111b) as perceived by endoscope (120) during the pivoting of line of sight (L); the distance ($d_e$) between distal end (126) of endoscope (120) and tissue surface (113) of lung (112); and/or the total sweep angle through which line of sight (L) is pivoted.

It will be appreciated that pivoting of line of sight (L) may be performed manually by a clinician manipulating the handle of endoscope (120), for example. In some versions, surgical visualization system (110) may be incorporated into a robotic system, such that line of sight (L) may be positionable by a robotic arm or other automated means. Moreover, while endoscope (120) has been described as being pivotable together with trocar (160) for facilitating pivoting of line of sight (L) about insertion point (P) relative to reference axis (R), in other versions at least a portion of camera (128), such as a movable lens, prism, mirror, or other optical element, may be pivotable relative to shaft (122) of endoscope (120) for facilitating pivoting of line of sight (L).

While surgical visualization system (110) is described herein in the context of visualizing nodules (111a, 111b)

embedded below surface (113) of lung (112) within thoracic cavity (150), it will be appreciated that surgical visualization system (110) may be utilized in any other surgical context, such as for visualizing other types of critical structures below a tissue surface in any other anatomical region, such as an abdominal cavity, for example.

III. Exemplary Method for Determining Critical Structure Depth

Having described exemplary features of surgical visualization system (110) above, an exemplary method (200) for determining the depths of one or more critical structures below a tissue surface will now be described in connection with FIGS. 9 and 10. While method (200) is shown and described for determining depth (D) of a nodule (N) below a tissue surface (S), method (200) may be employed in various other surgical applications for determining a depth of any other critical structure below a tissue surface in any anatomical region of a patient, such as for determining a depth ($d_A$) of ureter (11a) below surface (13) of uterus (12) and/or for determining depths ($d_{A1}$, $d_{A2}$) of nodules (111a, 111b) below surface (113) of lung (112).

Figure 9:
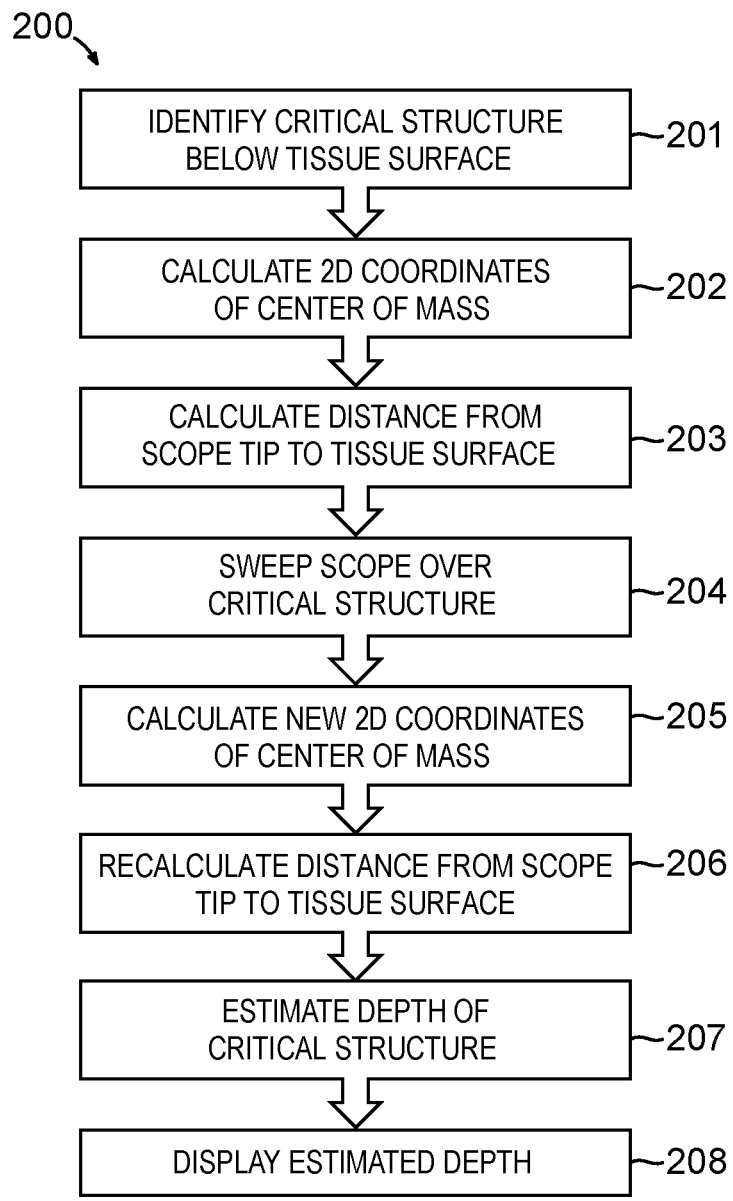
FIG. 9 depicts a flow diagram of an exemplary method for determining the depth of a critical structure below a tissue surface.

As shown in FIG. 9, method (200) begins with step (201), at which a critical structure, such as a nodule (N), is identified below a tissue surface, such as surface (S) of tissue (T). Step (201) may be performed via fluorescence and/or multispectral imaging using an endoscope, such as endoscope (E). Method (200) proceeds from step (201) to step (202), at which the 2-dimensional coordinates of a critical point, such as the center of mass or center of area, of the critical structure are calculated relative to the camera of the endoscope via a processor, such as processor (130), using image recognition software. For example, in instances where the line of sight of the camera is aimed directly at the critical point of the critical structure, the critical point may be at the origin of a coordinate system defined by the camera, as described above in connection with FIGS. 8A-8C.

Method (200) proceeds from step (202) to step (203), at which a distance from the distal end of the endoscope to the tissue surface, such as distance (Y), is calculated by the processor. Step (203) may be performed via structured/patterned light in a manner similar to that described above and/or in accordance with at least some of the teachings of U.S. Pat. Pub. No. 2017/0055819, entitled "Set Comprising a Surgical Instrument," published Mar. 2, 2017, issued as U.S. Pat. No. 11,033,182 on Jun. 15, 2021, and/or U.S. Pat. Pub. No. 2017/0251900, entitled "Depiction System," published Sep. 7, 2017, issued as U.S. Pat. No. 11,039,734 on Jun. 22, 2021, which are each incorporated by reference above.

Figure 10:
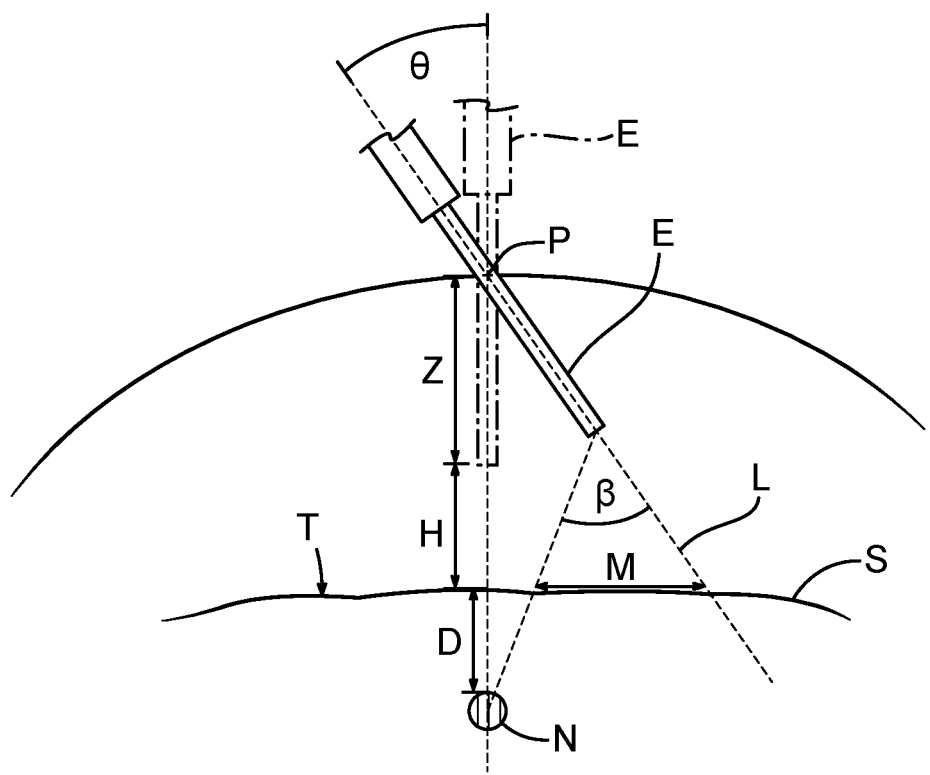
FIG. 10 depicts a schematic view of the surgical visualization system of FIG. 8A, showing pivoting of the imaging device for determining the depth of a critical structure below a tissue surface.

Method (200) proceeds from step (203) to step (204), at which the camera of the endoscope is swept over the critical structure to pivot its line of sight from a first orientation to a second orientation, as shown in FIG. 10, such that the critical structure appears to move as perceived by the endoscope. Sweeping of the camera over the critical structure may be achieved in any suitable manner, such as by pivoting the endoscope and/or pivoting at least a portion of the camera (e.g., a movable lens, prism, mirror, or other optical element thereof) relative to a shaft of the endoscope. Step (204) may be performed manually by the clinician or automatically, such as via a robotic system. In some cases, the camera may be swept through a predetermined sweep angle. In addition or alternatively, the camera may be swept such that its line of sight is pivoted through the critical structure. In cases where step (204) is performed manually, instructions for manually sweeping the camera may be presented to the clinician via a display, such as display (132), to assist the clinician with sweeping the camera in a proper manner for acquiring sufficient data to determine the depth of the critical structure. For example, such instructions may include a predetermined sweep angle and/or predetermined first and second orientations of the camera's line of sight.

Method (200) proceeds from step (204) to step (205), at which sweep parameters including the new 2-dimensional coordinates of the critical point of the critical structure are calculated relative to the camera of the endoscope via the processor, using image recognition software. In some versions, step (205) may include tracking the apparent motion of the critical point of the at least one critical structure as well as the apparent motion of the tissue surface as perceived by the endoscope while the camera is swept during step (204), such as via the image recognition software of the processor. In some versions, tracking the apparent motion of the tissue surface may be performed via the image recognition software by performing an ad hoc identification of a recognizable feature on the tissue surface, such as a dot or a fold, and by tracking the apparent motion of the identified feature. Step (205) may also include measuring the total sweep angle through which the line of sight of the camera is swept during step (204), such as via an IMU within the handle of the endoscope. Method (200) proceeds from step (205) to step (206), at which the distance from the distal end of the endoscope to the tissue surface previously calculated in step (203) is recalculated as it varies during step (204), which may be performed in the same manner as step (203). In some versions, step (205) and/or step (206) may be performed continuously during performance of step (204) to capture the desired sweep parameters.

Method (200) proceeds from step (206) to step (207), at which a depth of the critical structure below the tissue surface, such depth (D) of nodule (N), is estimated via the processor. Step (207) may be performed based on a predetermined relationship between the depth of the critical structure below the tissue surface, the difference in apparent motion between the critical structure and the tissue surface, the distance between the camera and the tissue surface, and/or the total sweep angle through which the line of sight of the endoscope is swept. In some versions, the depth of the critical structure may be estimated using the following equation:

$$D = ((H+Z)*\mathrm{Tan}(\theta) - M)*\mathrm{Tan}(90° - \beta + \theta)$$

where:

D is the depth of nodule (N) beneath surface (S) of tissue (T);

H is the distance from the distal tip of endoscope (E) to surface (S);

Z is the length of the portion of endoscope (E) between pivot point (P) and the distal tip of endoscope (E);

θ is the sweep angle through which endoscope (E) is pivoted about pivot point (P);

M is the distance along tissue (T) from the intersection of line of sight (L) of endoscope (E) and tissue (T) to the apparent location on surface (S) where the center of mass of nodule (N) appears on surface (S); and β is the angle between line of sight (L) of endoscope (E) and the line subtended from the distal tip of endoscope (E) to the apparent location of the center of mass of nodule (N) on surface (S).

However, it will be appreciated that any other suitable relationship between the monitored sweep parameters may be used to estimate the depth of the critical structure. In any event, method (200) proceeds from step (207) to step (208), at which the estimated depth of the critical structure is presented to the clinician, such as via display (132).

In some versions, a spectral source such as a light engine may project a chosen light pattern onto the patient's body habitus to be utilized by the processor and software to generate a 3D model of the body habitus to be used to inform the system of the dimensions and angles required for determination of the depth of the targeted structure. In addition or alternatively, an ultrasound device may be used to inform the system of the dimensions and angles required for determination of the depth of the targeted structure.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical visualization system comprising: (a) an endoscope comprising: (i) a shaft comprising a distal end, wherein the distal end is configured to be inserted into a cavity of a patient, (ii) a camera positioned at the distal end of the shaft for visualizing a first structure below a tissue surface within the cavity when the distal end is inserted into the cavity, wherein the camera defines a line of sight, wherein the camera is configured to be swept over the first structure about a pivot point; and (b) a processor in operative communication with the camera of the endoscope, wherein the processor is configured to: (i) monitor a plurality of sweep parameters when the camera is swept over the first structure about the pivot point, and (ii) estimate a depth of the first structure below the tissue surface based on the monitored plurality of sweep parameters.

Example 2

The surgical visualization system of Example 1, wherein the plurality of sweep parameters includes a first distance between the distal end and the tissue surface.

Example 3

The surgical visualization system of Example 2, wherein the plurality of sweep parameters further includes a second distance between the distal end and the pivot point.

Example 4

The surgical visualization system of Example 3, wherein the plurality of sweep parameters further includes a third distance between a first intersection of the tissue surface with the line of sight and a second intersection of the tissue surface with a line subtended from the distal end to a predetermined point of the first structure.

Example 5

The surgical visualization system of Example 4, wherein the plurality of sweep parameters further includes a first angle between the line of sight and the line subtended from the distal end to the predetermined point of the first structure.

Example 6

The surgical visualization system of Example 5, wherein the plurality of sweep parameters further includes a second angle through which the camera is swept about the pivot point.

Example 7

The surgical visualization system of Example 6, wherein the processor is configured to calculate the depth as $$D=((H+Z)*\mathrm{Tan}(\theta)-M)*\mathrm{Tan}(90°-\beta+\theta)$$

where:
D is the depth;
H is the first distance;
Z is the second distance;
θ is the second angle;
M is the third distance; and
β is the first angle.

Example 8

The surgical visualization system of any one or more of Examples 1 through 7, further comprising a display in operative communication with the processor, wherein the display is configured to present a tissue surface representation and a first structure representation.

Example 9

The surgical visualization system of Example 8, wherein the display is configured to augment the tissue surface representation and the first structure representation with a coordinate axis.

Example 10

The surgical visualization system of any one or more of Examples 7 through 9, wherein the display is configured to present the estimated depth of the first structure below the tissue surface.

Example 11

The surgical visualization system of any one or more of the preceding Examples, further comprising a trocar comprising a working channel, wherein the shaft of the endoscope is received within the working channel of the trocar when the distal end is inserted into the cavity.

Example 12

The surgical visualization system of Example 11, wherein the endoscope is pivotable together with the trocar about the pivot point when the shaft of the endoscope is received within the working channel of the trocar.

Example 13

The surgical visualization system of any one or more of the preceding Examples, wherein the endoscope further comprises an inertial measurement unit, wherein the camera is configured to be swept over the first structure about the pivot point through a sweep angle, wherein the inertial measurement unit is configured to detect the sweep angle.

Example 14

The surgical visualization system of any one or more of the preceding Examples, wherein the camera is configured to be swept over the first structure about the pivot point via pivoting of an optical element associated with the camera relative to the shaft of the endoscope.

Example 15

The surgical visualization system of any one or more of the preceding Examples, further comprising a light engine configured to illuminate the cavity of the patient for imaging by the camera and analysis by the processor.

Example 16

A surgical visualization system comprising: (a) a trocar comprising a working channel, (b) an endoscope at least partially received within the working channel of the trocar such that the endoscope is pivotable together with the trocar about an insertion point of the trocar, wherein the endoscope comprises: (i) a shaft comprising a distal end, wherein the distal end is configured to be inserted into a cavity of a patient, (ii) a camera positioned at the distal end of the shaft for visualizing a structure below a tissue surface within the cavity when the distal end is inserted into the cavity, wherein the camera defines a line of sight, wherein the camera is configured to be swept over the structure about the insertion point; (c) a processor in operative communication with the camera of the endoscope, wherein the processor is configured to: (i) monitor at least one sweep parameter when the camera is swept over the structure, and (ii) estimate a depth of the structure below the tissue surface based on the monitored at least one sweep parameter; and (d) a display in operative communication with the processor, wherein the display is configured to present the estimated depth of the structure below the tissue surface.

Example 17

A method for determining a depth of a structure below a tissue surface of a patient using an endoscope comprising a camera, the method comprising: (a) identifying the structure via the endoscope; (b) calculating a distance from a distal end of the endoscope to the tissue surface; (c) sweeping the camera of the endoscope over the structure; (d) monitoring at least one sweep parameter associated with the act of sweeping the camera of the endoscope over the structure; and (e) estimating the depth of the structure below the tissue surface based on the monitored at least one sweep parameter.

Example 18

The method of Example 17, wherein the act of monitoring at least one sweep parameter comprises monitoring relative motion between the endoscope and the structure during the act of sweeping the camera of the endoscope over the structure.

Example 19

The method of Example 18, wherein the act of monitoring at least one sweep parameter further comprises monitoring relative motion between the endoscope and the tissue surface during the act of sweeping the camera of the endoscope over the structure.

Example 20

The method of Example 19, wherein the act of sweeping the camera of the endoscope over the structure comprises sweeping the camera of the endoscope through a sweep angle, wherein the act of monitoring at least one sweep parameter further comprises monitoring the sweep angle.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application No. 17/375,593, entitled "Endoscope with Synthetic Aperture Multispectral Camera Array," filed on Jul. 14, 2021, published as U.S. Pub. No. 2023/0013884 on Jan. 19, 2023; U.S. patent application No. 17/375,615, entitled "Endoscope with Source and Pixel Level Image Modulation for Multispectral Imaging," filed on Jul. 14, 2021, published as U.S. Pub. No. 2021/0376444 Dec. 2, 2021; and/or U.S. patent application No. 17/375,281, entitled "Scene Adaptive Endoscopic Hyperspectral Imaging System," filed on Jul. 14, 2021, published as U.S. Pub. No. 2023/0020346 Jan. 19, 2023. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they may be designed to be used multiple times. Versions may, in either or both cases, be reconditioned for reuse after at least one use.

Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical visualization system comprising:
   (a) an endoscope comprising:
      (i) a shaft comprising a distal end, wherein the distal end is configured to be inserted into a cavity of a patient, and
      (ii) a camera positioned at the distal end of the shaft for visualizing a first structure below a tissue surface within the cavity when the distal end is inserted into the cavity, wherein the camera defines a line of sight, wherein the camera is configured to be swept over the first structure about a pivot point; and
   (b) a processor in operative communication with the camera of the endoscope, wherein the processor is configured to:
      (i) monitor a plurality of sweep parameters when the camera is swept over the first structure about the pivot point, and
      (ii) estimate a depth of the first structure below the tissue surface based on the monitored plurality of sweep parameters,
      wherein the plurality of sweep parameters includes a first distance between the distal end and the tissue surface,
      wherein the plurality of sweep parameters further includes a second distance between the distal end and the pivot point.

2. The surgical visualization system of claim 1, wherein the plurality of sweep parameters further includes a third distance between a first intersection of the tissue surface with the line of sight and a second intersection of the tissue surface with a line subtended from the distal end to a predetermined point of the first structure.

3. The surgical visualization system of claim 2, wherein the plurality of sweep parameters further includes a first angle between the line of sight and the line subtended from the distal end to the predetermined point of the first structure.

4. The surgical visualization system of claim 3, wherein the plurality of sweep parameters further includes a second angle through which the camera is swept about the pivot point.

5. The surgical visualization system of claim 4, wherein the processor is configured to calculate the depth as $$D=((H+Z)*\text{Tan}(\theta)-M)*\text{Tan}(90°-\beta\theta)$$

where:
D is the depth;
H is the first distance;
Z is the second distance;
θ is the second angle;
M is the third distance; and
β is the first angle.

6. The surgical visualization system of claim 1, further comprising a display in operative communication with the processor, wherein the display is configured to visually present a tissue surface representation and a first structure representation.

7. The surgical visualization system of claim 6, wherein the display is configured to visually present the tissue surface representation and the first structure representation relative to a coordinate axis.

8. The surgical visualization system of claim 6, wherein the display is configured to visually present the estimated depth of the first structure below the tissue surface.

9. The surgical visualization system of claim 1, further comprising a trocar comprising a working channel, wherein the shaft of the endoscope is received within the working channel of the trocar when the distal end is inserted into the cavity.

10. The surgical visualization system of claim 9, wherein the endoscope is pivotable together with the trocar about the pivot point when the shaft of the endoscope is received within the working channel of the trocar.

11. The surgical visualization system of claim 1, wherein the endoscope further comprises an inertial measurement unit, wherein the camera is configured to be swept over the first structure about the pivot point through a sweep angle, wherein the inertial measurement unit is configured to detect the sweep angle.

12. The surgical visualization system of claim 1, further comprising a light engine configured to illuminate the cavity of the patient for imaging by the camera and analysis by the processor.

13. A surgical visualization system comprising:
   (a) a trocar comprising a working channel,
   (b) an endoscope at least partially received within the working channel of the trocar such that the endoscope is pivotable together with the trocar about an insertion point of the trocar, wherein the endoscope comprises:

(i) a shaft comprising a distal end, wherein the distal end is configured to be inserted into a cavity of a patient, and (ii) a camera positioned at the distal end of the shaft for visualizing a structure below a tissue surface within the cavity when the distal end is inserted into the cavity, wherein the camera defines a line of sight, wherein the camera is configured to be swept over the structure about the insertion point;

(c) a processor in operative communication with the camera of the endoscope, wherein the processor is configured to:

(i) monitor at least one sweep parameter when the camera is swept over the structure, (ii) calculate a distance between the distal end and the insertion point. and (iii) estimate a depth of the structure below the tissue surface based on the monitored at least one sweep parameter and the calculated distance between the distal end and the insertion point; and (d) a display in operative communication with the processor, wherein the display is configured to visually present the estimated depth of the structure below the tissue surface.

14. A method for determining a depth of a structure below a tissue surface of a patient using an endoscope comprising a camera, the method comprising:

(a) identifying the structure via the endoscope;

(b) calculating, via a processor a first distance from a distal end of the endoscope to the tissue surface;

(c) sweeping the camera of the endoscope over the structure about a pivot point;

(d) monitoring, via the processor, at least one sweep parameter associated with the act of sweeping the camera of the endoscope over the structure;

(e) calculating, via the processor, a second distance between the distal end of the endoscope and the pivot point; and (f) estimating, via the processor, the depth of the structure below the tissue surface based on the monitored at least one sweep parameter and the calculated second distance between the distal end of the endoscope and the pivot point.

15. The method of claim 14, wherein the act of monitoring at least one sweep parameter comprises monitoring, via the processor, relative motion between the endoscope and the structure during the act of sweeping the camera of the endoscope over the structure.

16. The method of claim 15, wherein the act of monitoring at least one sweep parameter further comprises monitoring, via the processor, relative motion between the endoscope and the tissue surface during the act of sweeping the camera of the endoscope over the structure.

17. The method of claim 16, wherein the act of sweeping the camera of the endoscope over the structure comprises sweeping the camera of the endoscope through a sweep angle, wherein the act of monitoring at least one sweep parameter further comprises monitoring, via the processor, the sweep angle.

18. The method of claim 14, wherein the act of sweeping the camera of the endoscope over the structure is performed after the act of calculating the first distance.

19. The method of claim 14, wherein the act of monitoring the at least one sweep parameter is performed continuously during the act of sweeping the camera of the endoscope over the structure.

20. The surgical visualization system of claim 1, wherein the camera is fixedly secured to the distal end of the shaft.

* * * * *